United States Patent [19]

Forbes et al.

[11] Patent Number: 5,578,359

[45] Date of Patent: Nov. 26, 1996

[54] MAGNETIC SHIELDING GARMENT FOR ELECTRO-BIOLOGIC MEASUREMENTS

[75] Inventors: A. Dean Forbes; Robert A. Piety, both of Palo Alto, Calif.

[73] Assignee: Hewlett Packard Company, Palo Alto, Calif.

[21] Appl. No.: 346,054

[22] Filed: Nov. 29, 1994

[51] Int. Cl.$^6$ .............................. A61B 19/08; D06H 7/00
[52] U.S. Cl. ..................... 428/131; 2/2; 26/7; 128/849; 139/291 R; 139/425 R; 428/226
[58] Field of Search ................................... 428/226, 131; 2/2; 139/425 R, 291 R; 128/849; 26/7

[56] References Cited

U.S. PATENT DOCUMENTS

| 4,030,892 | 6/1977 | Mendesohn | 428/226 |
|---|---|---|---|
| 4,097,631 | 6/1978 | Wilken | 428/226 |
| 4,126,287 | 11/1978 | Mendelsohn | 245/8 |
| 5,045,637 | 9/1991 | Sato | 174/35 MS |
| 5,071,699 | 12/1991 | Pappas | 428/226 |
| 5,215,813 | 6/1993 | Hartman et al. | 428/226 |
| 5,215,816 | 6/1993 | Shibata et al. | 428/226 |
| 5,217,796 | 6/1993 | Kasai | 428/226 |
| 5,260,128 | 11/1993 | Ishii | 428/328 |
| 5,273,822 | 12/1993 | Hayashi et al. | 428/226 |

OTHER PUBLICATIONS

*Chemical Abstracts* 93:270 145.
*Chemical Abstracts* 122 149 595.

Primary Examiner—James C. Cannon

[57] ABSTRACT

An electromagnetic shielding garment comprising amorphous alloy strips or strands woven together. The woven material or sheet can be reenforced by bonding it to a flexible material such as plastic. This garment is effective in shielding a patient from extraneous electromagnetic radiation to allow sensitive medical measurements to be taken with minimal interference.

8 Claims, 2 Drawing Sheets

MAGNETIC SHIELDING GARMENT FOR ELECTRO-BIOLOGIC MEASUREMENTS

FIELD OF THE INVENTION

This invention relates to a method of magnetically shielding sensitive medical measurements, and more specifically for providing a magnetic-shielding garment for electro-biologic measurements.

BACKGROUND

Sensitive electronic measurements can be disturbed by extraneous electro-magnetic interference. Electro-magnetic interference is generated from a variety of sources including CRTs, electrical equipment and power lines. To minimize the disturbances that these sources of electromagnetic interference introduce to sensitive measurements, electromagnetic shielding must be provided. In medical treatment environments where sensitive measurements like electrocardiographic data acquisition have to be made, a form of electromagnetic shielding must be provided which does not inhibit the medical personnel. The shielding should not hamper or prevent the medical practitioner from being able to perform critical medical functions.

One method to reduce the electromagnetic interference in a medical environment is to provide an entire room that is magnetically shielded with high permeability alloys. This is an effective solution to shielding. However, the disadvantages with this approach are the high cost involved in building a special room and the need to ensconce the patient in it.

Another method of shielding includes coffin-like chambers or cylinders made from similar alloys. These solutions are less costly than shielding an entire room but are undesirable for other reasons. Putting the patient in such a device does not allow for quick access to the patient in emergency situations. This approach can also be uncomfortable to the patient if he or she is claustrophobic or uncomfortable in tight spaces. The situation can be exacerbated if the patient is in pain, injured or critically ill.

High magnetic permeability sheets and associated shielding materials as suggested in U.S. Pat. No. 5,045,637 and U.S. Pat. No. 5,260,128 have been designed for aiding in the manufacturing of magnetically shielded enclosures. The enclosures can be designed to keep electromagnetic radiation in or out. Examples of enclosures include electronic test instrumentation and electromagnetically shielded rooms.

The optimal device for shielding of extraneous electromagnetic signals in the medical environment would shield effectively, be inexpensive, easy to use and be minimally distressing to the patient.

SUMMARY OF INVENTION

This invention provides a garment for shielding the patient. This approach is much less expensive than prior solutions. The garment takes up very little space and is minimally distressing to the patients. The garment is constructed to significantly reduce the patient's exposure to electromagnetic radiation while maintaining accessibility to the patient which may be required in a hospital environment. An electromagnetic shielding garment has the advantages that it is light weight, portable and inexpensive.

The garment can be made up of amorphous alloy strips or wires which have been woven together to create a flexible fabric. In one application of the present invention, the amorphous alloy strips are Magnetic Alloy 2705M manufactured by Metglas® of Parsippay, N.J. However, any flexible fabric made of a high permeability alloy that can withstand repeated flexing and stressing without losing its magnetic properties is suitable. The permeability of the amorphous alloy material is about 100,000 µz at frequencies of less than 1000 hertz.

In another application of the present invention, strands made from an amorphous alloy are woven, bonded or encapsulated to provide a flexible magnetic shielding fabric. The fabric is able to withstand mechanical stressing and flexing without losing its shielding properties.

A woven fabric of amorphous alloy material has some advantages over a continuous sheet formed out of amorphous alloy materials. Weaving amorphous alloy strands or strips yields a material which is similar in structure to the conventional fabrics used to manufacture clothing. The shielding garment is made to shield a human patient. The patient is shielded by wrapping or fitting the garment about the patient. A woven fabric of amorphous material will adjust and give to more comfortably fit on a patient's body. A garment made of a non-fabric like amorphous alloy sheet would be more rigid and not fit as comfortably as a garment made of a woven amorphous alloy structure. A continuous thin sheet of amorphous material will probably include some type of binding material. Therefore, it will be stiffer than a fabric or weave made of strands or strips of the same material.

The garment of this invention is formed by first producing a sheet of amorphous alloy fabric. A hole is then cut in the sheet to allow a patient's head to pass through it. Slots are cut out of the sheet to allow the sheet to be wrapped around and encapsulate the patient.

An alloy like Metglas® is typically used for electromagnetic shielding of sources of electromagnetic interference. Typical sources of interference include transformers, motors and power supplies. Such amorphous metal strips are based on alloys of iron, nickel and cobalt. The strips comprise a variety of ferromagnetic compositions that combine magnetic softness with high mechanical strength and hardness and can be stressed and flexed without losing their magnetic properties.

DETAILED DESCRIPTION

This invention encompasses a garment for electromagnetically shielding a patient. The shielding allows sensitive medical measurements to be made with reduced levels of interference from electromagnetic signals. Electromagnetic interference is commonly present in laboratories, hospitals and industrialized areas. All of these locations are places in which one may desire to make sensitive medical measurements on a patient. Alternating current power lines are generally the source of the magnetic interference. The typical power line interference is comprised of a fundamental frequency of 50 or 60 Hertz, and the first few harmonics of the fundamental. Other sources of strong interfering electromagnetic fields are motors, CRT monitors and power supplies.

Figure 1:
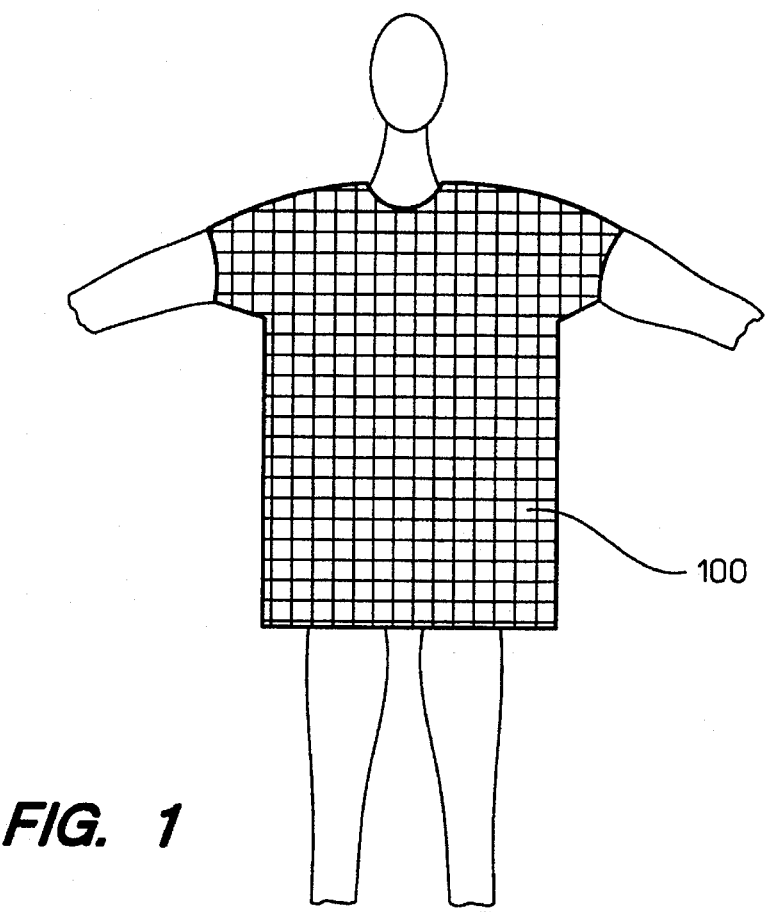
FIG. 1 shows a shielding garment as worn by a person.

As shown in FIG. 1, the garment 100 wraps around the patient wearing it, and it should be made out of a flexible material. Continual flexing of most shielding materials will reduce their permeability. An amorphous alloy is chosen for this invention because of its tolerance to mechanical flexing and stressing. Amorphous alloys also have excellent magnetic shielding properties. Amorphous alloys have a high magnetic permeability of up to 100,000 μz at frequencies of less than 1000 hertz. They are light weight, have acceptable handling properties and offer construction workability. Amorphous alloys also have high mechanical elasticity. Therefore, if the material is deformed by a stress imposed during handling, the shape is restored when the stress is released.

Figure 2:
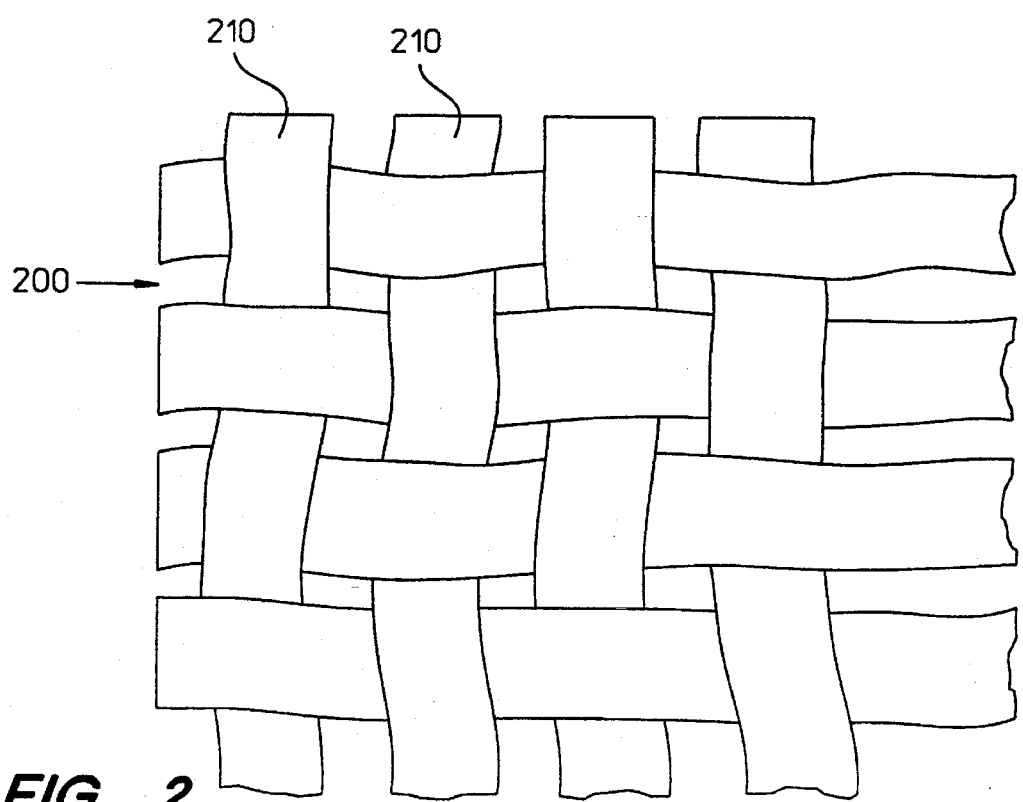
FIG. 2 shows an amorphous alloy metal strips weave.

One aspect of this invention includes an interleaved weave of amorphous alloy strips 210 as shown in FIG. 2. The strips 210 are woven together to form a large rectangular sheet 200. The final configuration can be composed of many sheets 200 layered on top of each other. The amount of shielding will be greater as the number of sheets 200 is increased. Experimentally, it has been found that each sheet 200 of fabric made from 0.0008" Metglas® provides about ⅔ dB of magnetic field strength attenuation at a magnetic field frequency of between 60–300 Hz. The garment 100 can be manufactured out of the required number of sheets 200 to obtain the desired amount of magnetic attenuation without unacceptably compromising flexibility and weight. The plurality of sheets 200 can be laminated between or bonded to plastic, to enhance the physical strength and durability. The strips 210 of FIG. 3 could be replaced with strands of amorphous alloy material. This will provide for a sheet of amorphous alloy material which is similar in structure to conventional fabric. With this structure, the amorphous alloy sheet can be used to produce garments in a fashion similar to the processes used to make clothing out of conventional fabric.

Figure 3:
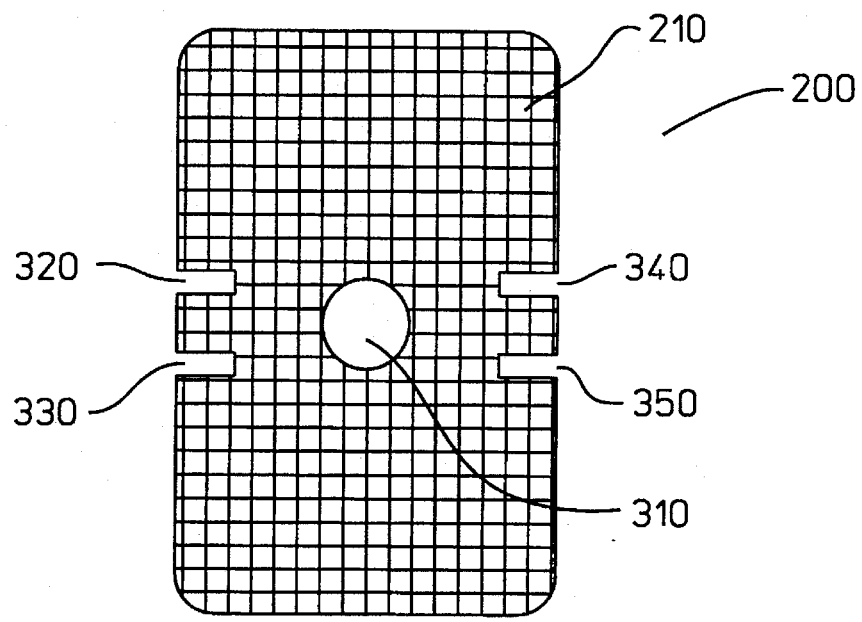
FIG. 3 shows an amorphous alloy strip sheet.
Figure 4:
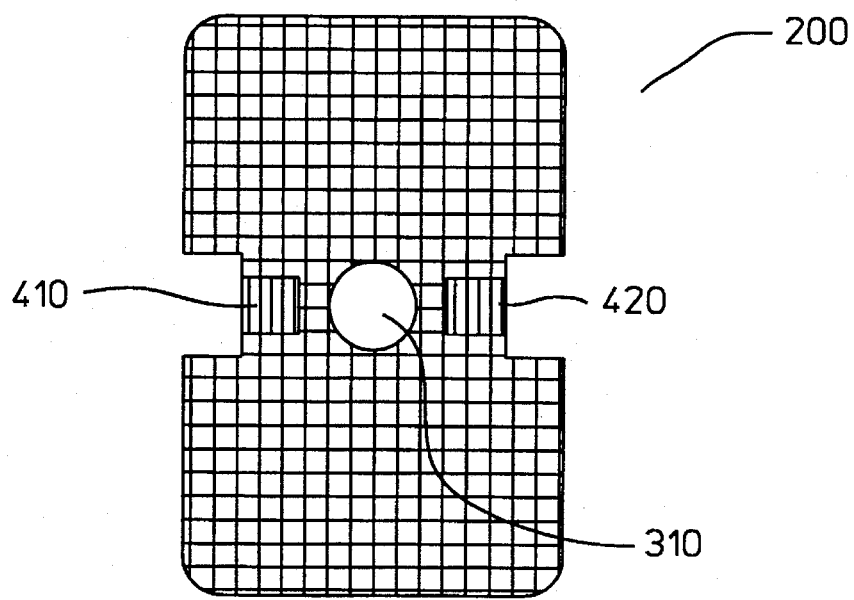
FIG. 4 shows an amorphous alloy strip shielding garment.

As shown in FIG. 3, an opening 310 is cut in the center of the sheet 200 for the patient's head to fit through. Four slots 320, 330, 340 and 350 are cut in the sheet 200 and the material is folded back to allow the patient's arms to extend out. FIG. 4 shows that the portions remaining from the cut out portions of the sheet are folded back to provide extra shielding 410, 420 over the patient's shoulders. The garment 100 wraps around the patient and forms a shield which is shaped like a cylinder. Low frequency magnetic fields generally penetrate the open ends of a magnetic shielding material cylinder to a depth of approximately the diameter of the cylinder. Therefore, the length of the sheet 200 from top to bottom is selected so that magnetic fields will not intrude excessively through the required openings. Most ECG and other medical measurements are focused on the torso. For adequate shielding of the torso during these measurements, the garment length should be long enough to reach the mid-thigh or knee area. This will ensure that the torso is away from the bottom opening of the garment by at least the diameter of the cylindrical shape formed by the garment. The opening of the garment for the head and arms must be minimized in size to reduce the magnetic field penetration through them. Specific garment configurations which include sleeves or collars can be fabricated to further reduce magnetic field entry through arm and head openings if necessary.

Other features or configurations of the shielding garment can implemented. The woven structure of the amorphous alloy fabric allows flexibility in the form of the final garment configuration.

We claim:

1. A garment functioning to magnetically shield the wearer thereof and minimizing electromagnetic interference while maintaining accessibility to the torso of said wearer during sensitive electronic measurement thereof comprising a sheet of at least one layer of a flexible, high magnetic permeability amorphous alloy fabric.

2. The magnetic shielding garment as recited in claim 1, wherein the flexible amorphous alloy fabric comprises a plurality of amorphous alloy strips which have been woven together.

3. The magnetic shielding garment as recited in claim 1, wherein the flexible amorphous alloy fabric comprises a plurality of amorphous alloy strands which have been woven together.

4. The magnetic shielding garment as recited in claim 1, wherein the sheet is laminated with a plastic coating to increase the mechanical strength of the sheet.

5. The magnetic shielding garment as recited in claim 1, wherein the sheet is bonded to a flexible material to increase the mechanical strength of the sheet.

6. The magnetic shielding garment as recited in claim 1, wherein the sheet has a center, and an opening exists in the center of the sheet to allow a patient's head to pass through the sheet.

7. The magnetic shielding garment as recited in claim 6, wherein the sheet has select portions cut out to allow the garment to be wrapped around the patient.

8. A method of fabricating a garment functioning to magnetically shield the wearer thereof and minimizing electromagnetic interference while maintaining accessibility to the torso of said wearer during sensitive electronic measurement thereof comprising the steps of:

weaving amorphous alloy strips to form a sheet of magnetic shielding fabric;

cutting an opening in the center of the magnetic shielding fabric for receiving a patient's head; and cutting portions out of the sheet and folding the residual portions back to provide added shielding over the patient's shoulders.

* * * * *